United States Patent [19]

Carrie et al.

[11] Patent Number: 5,011,283
[45] Date of Patent: Apr. 30, 1991

[54] FLOW CELL SUPPORT DEVICE

[75] Inventors: Tony R. Carrie, Evansville; Robert A. Newton, Owensville, both of Ind.

[73] Assignee: Bristol-Myers Squibb Co., New York, N.Y.

[21] Appl. No.: 461,879

[22] Filed: Jan. 8, 1990

[51] Int. Cl.⁵ ............................................. G01N 21/01
[52] U.S. Cl. ...................................... 356/246; 250/428
[58] Field of Search ................. 356/244, 246; 250/428; 248/346, 678

[56] References Cited

U.S. PATENT DOCUMENTS

| | | | |
|---|---|---|---|
| 2,637,817 | 5/1953 | Herbert | 356/246 |
| 2,864,279 | 12/1958 | Phifer | 356/244 |
| 2,970,216 | 1/1961 | McGrath | 356/246 |

Primary Examiner—Richard A. Rosenberger
Attorney, Agent, or Firm—Robert H. Uloth

[57] ABSTRACT

A support device for a workpiece, such as a spectrophotometric flow cell is provided. The device includes a base plate, a mounting bar attached to the base plate, a support arm slidably mounted on the base plate/mounting bar assembly, an adjustment plug contained in an elongate cavity formed in the support arm, and a workpiece rotatably friction mounted on the adjustment plug. With the base plate mounted horizontally, the orientation and position of the work piece may be adjusted horizontally by sliding the support arm along the mounting bar, vertically by moving the adjustment plug within the elongate cavity and rotationally by rotating the workpiece, which is retained in its new position by the friction mount.

9 Claims, 4 Drawing Sheets

FLOW CELL SUPPORT DEVICE

FIELD OF THE INVENTION

The present invention is directed generally to a support device for adjustable and rotatably securing a workpiece. More particularly, the present invention is directed to a support device for adjustable and rotatably securing a spectrophotometric flow cell. Most specifically, the present invention is directed to a support device for a spectrophotometric flow cell in which the flow cell position or orientation with respect to the spectrophotometric device may be easily changed either linearly or radially by adjustment of the movable elements of the support device. These movable elements include a support arm slidably mounted on a mounting bar and an adjustment plug located in an elongated cavity in the support arm. The mounting bar extends vertically from a base plate which is horizontally and fixedly mounted to a support surface and onto which is mounted the mounting bar.

BACKGROUND OF THE INVENTION

Spectral analysis techniques have historically been used to characterize and quantify compositions of interest. A cost-effective way to utilize spectrophotometers for liquid samples is to use flow-through cells. However, it is difficult to design and mount flow-through cells for spectrophotometers that provide the necessary flow characteristics and ease of mounting necessary to successfully convert a spectrophotometer where samples are introduced manually via a cuvette to one where air-segmented samples may flow and be de-bubbled immediately prior to being introduced into the light path. This is evidenced by the fact that few vendors provide this technology for ultra-violet and visible wavelengths. The capability to use a flow-through cell would expand the marketability of any spectrophotometer that possessed it.

The prior art generally provides for spectrophotometric flow cell support devices. For example, U.S. Pat. No. 2,637,817 to Herbert provides for a positioning adaptor for an infrared spectroscopic cell which provides an adjustment mechanism for the length of the infrared path through the liquid being measured. The adjustment is limited to a linear change along one axis; further, no rotational change of cell orientation is possible. U.S. Pat. No. 2,864,279, to Phifer, discloses a spectrophotometer cell holder which does not allow for any adjustment of the cell position once mounted on the holder. U.S. Pat. No. 2,970,216, to Magrath, discloses a sample cell for spectroscopic apparatus which, like the Herbert device, permits only unidirectional, linear adjustment of the cell. None of these devices have the capability of providing multidirectionally and rotatably adjustable support for a conventional T-type flow-through cell.

It will accordingly be appreciated that there is a need for a flow cell support device which is manipulatable to adjust the position and orientation of a T-type flow-through cell which is utilized in modern spectrophotometry because of its higher resolution with lower dead volume.

SUMMARY OF THE INVENTION

It is an object of the present invention to provide a support device for adjustable and rotatably securing a workpiece.

A further object of the present invention is to provide a support device for a spectrophotometric cell.

Another object of the present invention is to provide a support device for a T-type, flow-through spectrophotometric cell.

Yet a further object of the present invention is to provide a support device for a T-type, flow-through spectrophotometric cell which, by manipulation of its elements, adjusts the position and orientation of the supported cell.

Still another object of the present invention is to provide a support device for a T-type, flow-through spectrophotometric cell which, by manipulation of its elements, adjusts the position of the supported cell along a first axis and a second perpendicular axis and further adjusts the rotational orientation of the supported cell about a second axis parallel to the first axis within the plane formed by the first and second axes.

Briefly, the support device of the present invention includes a base plate having a front surface, a mounting bar attached to the base plate at the front surface, a support arm having an elongate hollow portion formed therein releasably attached to the mounting bar and extending perpendicularly from the front surface of the base plate, and an adjustment plug received in an elongate hollow portion formed in the support arm. An adjustment rod extends through the elongated hollow portion of the support arm and through an aperture formed in the adjustment plug. The cell is rotatably connected to the adjustment plug, abutting a friction element and extending outwardly from the adjustment plug.

The support arm is releasably connected to the mounting bar and therefore slides along the mounting bar, allowing positional adjustment of the supported cell in a first linear direction. The adjustment plug is movably received in the elongate hollow portion of the support arm, allowing positional adjustment of the support cell along a second axis which is perpendicular to first axis. The connection of the supported cell to the adjustment plug allows rotational adjustment of the cell along an axis normal to the front face of the adjustment plug.

By manipulating the elements of the support device, the exact position and orientation of the mounted cell can be easily and accurately changed or adjusted as necessary. The device therefore provides a spectrophotometric mounting cell apparatus which is easily installable and simply manipulated, and further provides a structure for holding the mounted cell which provides for a more varied and accurate adjustment of cell position and orientation then heretofore known.

BRIEF DESCRIPTION OF THE DRAWINGS

While the novel features of the support device of the present invention are set forth with particularity in the appended claims, a full and complete understanding of the invention may be had by referring to the detailed description of the preferred embodiment, as set forth below, and the accompanying drawing in which;

DESCRIPTION OF THE PREFERRED EMBODIMENT

It is initially noted that the references to direction, position and axial orientation provided below are made with respect to the orientation of the elements in the attached drawing FIGURES.

Figure 1:
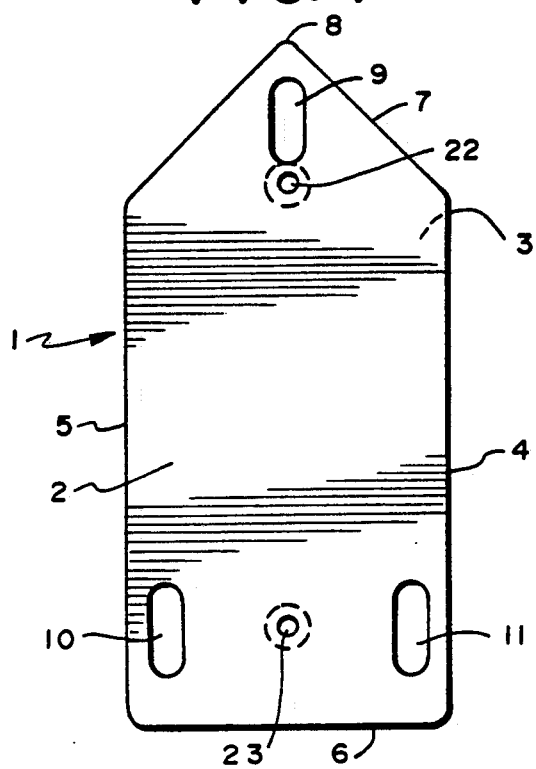
FIG. 1 is a top plan view of the base plate of the present invention.

FIG. 1 illustrates a base plate of the present invention. The base plate 1 includes a front surface 2, a back surface 3 parallel to the front surface, a right side edge 4, a left side edge 5, a bottom straight edge 6 and a top edge 7. Preferably, the top edge 7 will be tapered inwardly from the side edges to form a rounded point 8 to reduce the overall size of and increase ease of installation of the support device.

The base plate 1 preferably includes a plurality of mounting bores 9, 10 and 11 extending through the thickness of the base plate 1 and along an axis normal to the front and back surfaces. Top mounting bore 9 and bottom mounting bores 10 and 11 may be utilized for attaching base plate 1 by any conventional means to a mounting surface 12. Base plate is preferably formed from a thin lightweight metal alloy sheet.

Figure 2:
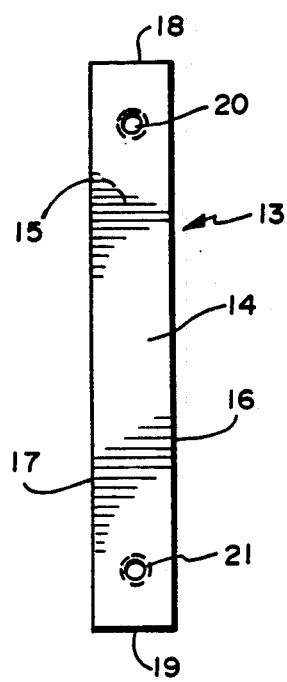
FIG. 2 is a top plan view of the mounting bar of the present invention.
Figure 3:
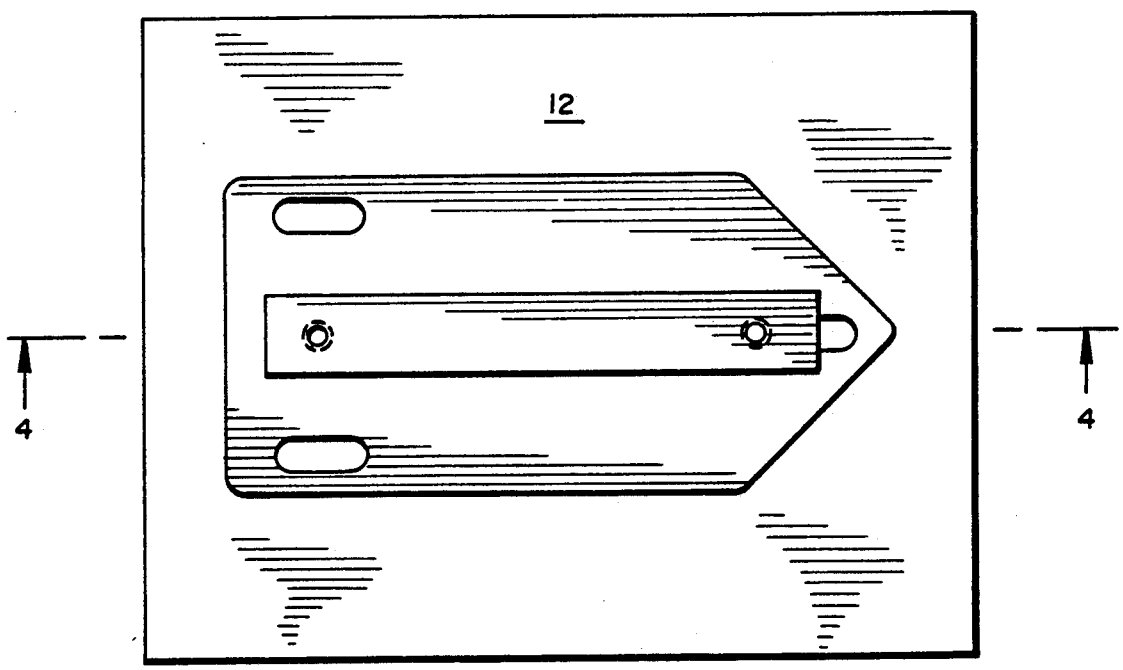
FIG. 3 is top plan view of the mounting bar and base plate of the present invention, mounted on a support surface.
Figure 4:
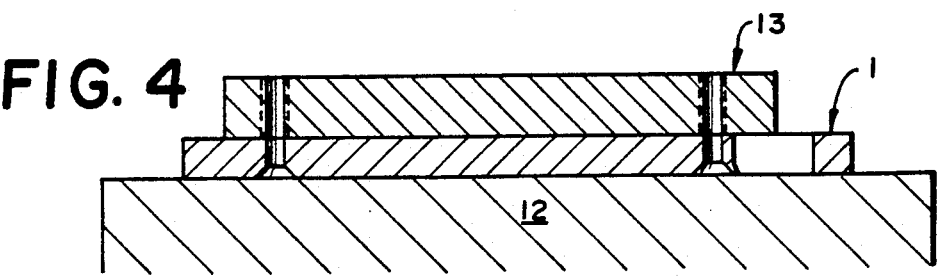
FIG. 4 is a cross-section view of the assembly of FIG. 3 taken along line 4—4.

Mounted on base plate 1 along its front surface 2 is mounting bar 13, illustrated in FIG. 2. Mounting bar 13, preferably rectangular in cross-section, includes a front face 14, back face 15, right side face 16, left side face 17, top end 18 and bottom end 19. Mounting bar 13 may be formed integrally with base plate 1 or may be separately formed and attached thereto. If separate attaching elements are required, mounting bar 13 preferably includes bar apertures 20 and 21. Base plate 1 preferably includes base apertures 22 and 23 which align with apertures 20 and 21 when the base plate 1 and mounting bar 13 are assembled, as shown in FIGS. 3 and 4. When assembled with the base plate, the mounting bar 13 is preferably centered between the right edge 4 and the left edge 5 of the base plate 1 and extends from the bottom of the top mounting bore 9 to the bottom straight edge 6 of the base plate 1. The mounting bar 13 may be attached to the front surface 2 of the base plate 1 by any conventional means, including adhesives or mechanical means, including rivets, pins or screws which extend through aligned bar apertures 20 and 21 and base apertures 22 and 23. Preferably, the mounting bar 13 and base plate 1 are separately formed and are assembled with screws.

Mounting bar 13 is preferably formed of the same lightweight alloy material as base plate 1 and in preferred form is an elongated rectangular bar.

Figure 5:
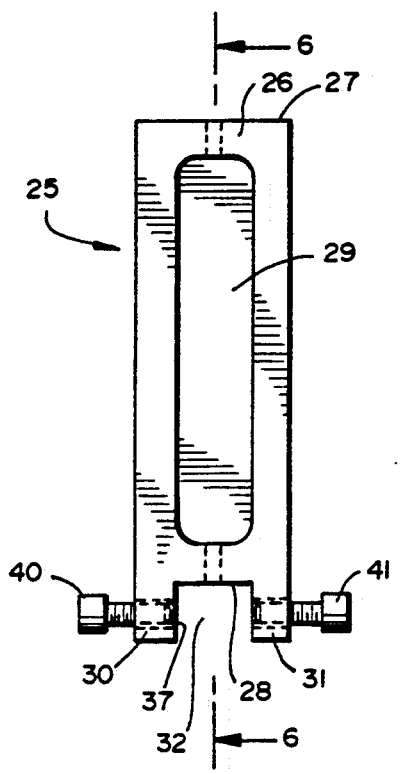
FIG. 5 is a front elevational view of the support arm of the present invention.
Figure 6:
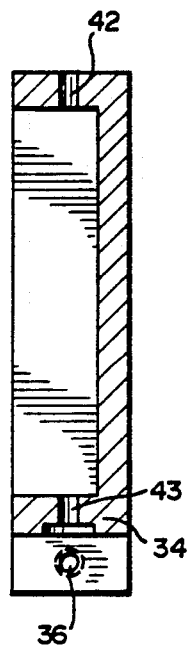
FIG. 6 is a cross sectional view of the support arm of FIG. 5 taken along line 6—6.

Support arm 25, as seen in FIGS. 5 and 6, generally includes front face 26, upward face 27 and downward face 28. Elongate cavity 29 extends inwardly into the support arm 25 in a direction perpendicular to the front face 26. Support legs 30 and 31 extend outwardly from downward face 28 in a direction normal to the face 28, thereby forming a slot 32. Elongate cavity 29 is preferably U-shaped in cross-section for receiving the adjustment plug 50, as described below, and extends from near the upward face 26 to near the slot 32. Slot 32 is preferably rectangular in cross-section for receiving mounting bar 13 when the support device is assembled.

Preferably, a support aperture 36 extends from an inward face 37 of support leg 30 outwardly through the support leg 30. A similar support aperture 38 extends through support leg 31. These apertures are preferably threaded for receiving set screws 40 and 41, which extend into the apertures and through the support legs to abut side faces 16 and 17 of the mounting bar 13 when assembled.

Support arm 25 preferably includes an upper adjustment rod aperture 42 extending from the upward face 27 of the support arm 25 inwardly toward the cavity 29 and normal to the face 27 of the support arm 25. A lower adjustment rod aperture 43 extends from the elongate cavity 29 through the portion 34 of the support arm 29 between the cavity 32 and the slot 32. Adjustment rod apertures 42 and 43 receive an adjustment rod 45, which extends from above the upward face of the support arm 25 through aperture 42, through the cavity 29 and through the lower aperture 43. A locking nut 46 is attached to the lower end of adjustment rod 45 while knob 4 is attached to the top end 48 of rod 45. For this reason, at least the ends of the adjustment rod 45 one threaded; preferably the entirety of adjustment rod 45 is threaded for reasons described below.

Figures 8, 9, 10:
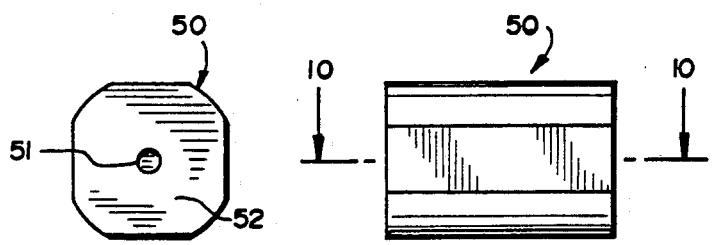
FIG. 8 is a bottom plan view of the support arm assembly of the present invention.
FIG. 9 is a front plan view of the adjustment plug of the present invention.
FIG. 10 is a side elevational view of the adjustment plug of the present invention.
Figure 10A:
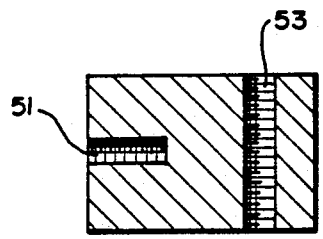
FIG. 10A is a cross-sectional view of the adjustment plug taken along the 10—10 of FIG. 10.

Mounted along the length of adjustment rod 45 is an adjustment plug 50, illustrated in FIGS. 9 and 10. Adjustment plug 50 includes a workpiece receiving aperture 51, preferably threaded, which extends partially into the plug in a direction normal to a friction face 52 and an adjustment rod receiving aperture 53, preferably threaded, which extends through the thickness of the plug and extends along an axis perpendicular to the workpiece receiving aperture 51. Preferably the plug 50 is octagonal in cross section.

Figure 7:
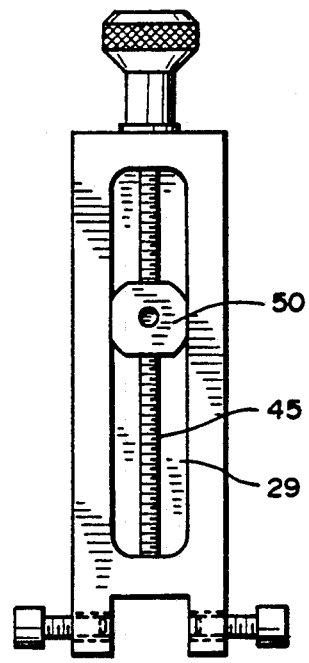
FIG. 7 is a front elevation view of the support arm assembly of the present invention.
Figure 11:
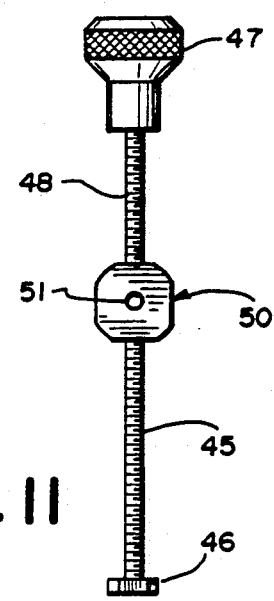
FIG. 11 is a front plan view of the adjustment rod assembly of the present invention.

As illustrated in FIGS. 7 and 11, adjustment plug 50 is contained in elongate cavity 29 and is oriented so that friction face 52 is exposed outwardly from the cavity 29 and so that the longitudinal axis of the adjustment rod receiving aperture 53 extends parallel to the longitudinal axis of the elongated cavity 33. Adjustment rod 45 extends through upper adjustment aperture 42 in support arm 25, through adjustment rod receiving aperture 53 in plug 50 and through the lower adjustment aperture 43 in support arm 25. As assembled, adjustment rod 45 threadedly engages adjustment rod aperture 42 in plug 50 and, when rotated, actuates linear movement of the plug 50 along and within elongate cavity 29 in support arm 25.

This support arm assembly, illustrated in FIG. 7, is slidably and releasably mounted on the base plate which has mounting bar 13 mounted thereon and which was described previously and illustrated in FIGS. 3 and 4. Slot 32 formed by downwardly extendedly support legs 30 and 31 receives mounting bar 13 while the support legs rest on the front surface 2 of base plate 1. As assembled, support arm 25 is slidably mounted on base plate 1 along the length of mounting bar 13. Once the desired position of the support arm 25 is selected, set screws 40 and 41 threadedly engage support apertures 36 and 38 in legs 40 and 41 and, when rotated sufficiently, abut mounting bar 13.

Figure 12:
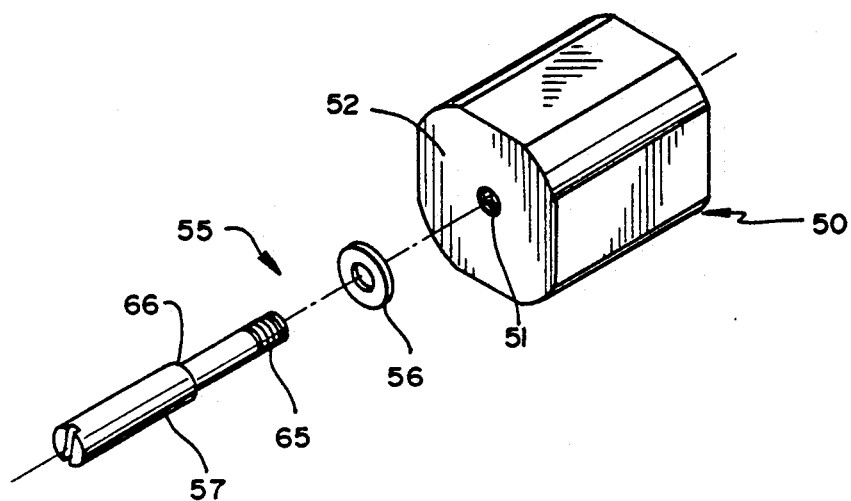
FIG. 12 is an exploded perspective view of the friction securing mounting of the present invention.
Figure 13:
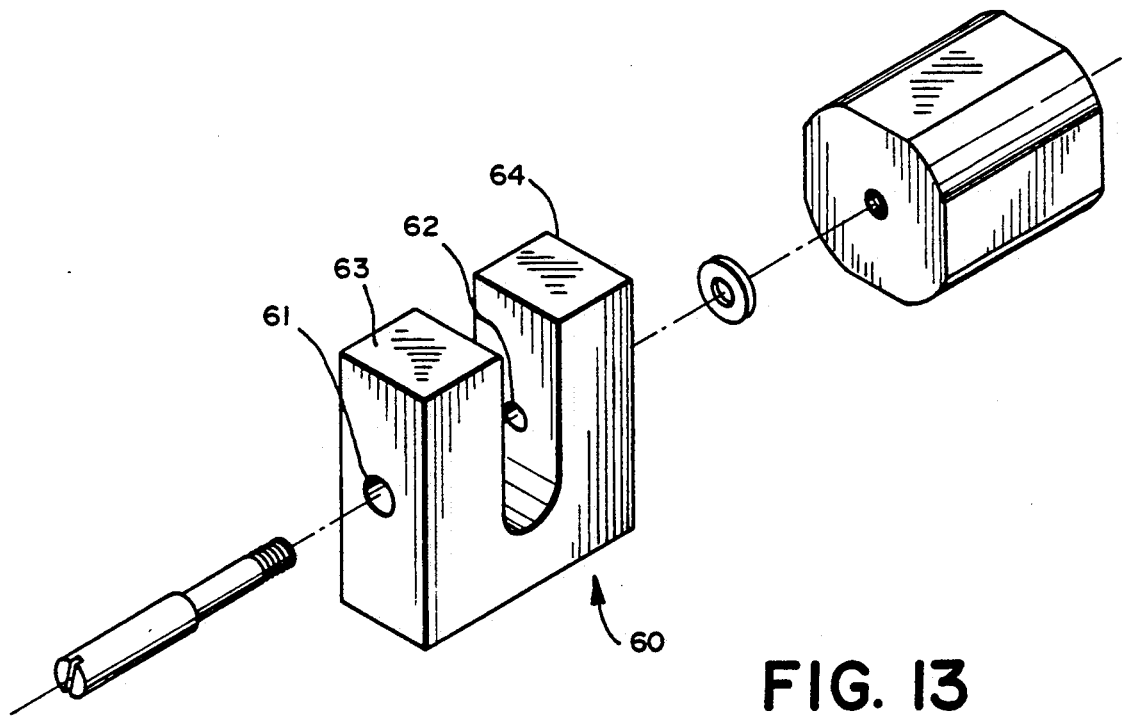
FIG. 13 is an exploded perspective view of the assembled friction securing mount and workpiece of the present invention.

As seen in FIGS. 12 and 13, aperture 51 in plug 50 receives a rotatable friction securing mount 55, including a friction element 56 for engaging friction face 52 and a securing element 57 which extends into aperture 51 for rotatably securing a workpiece 60 and friction element 56 to plug 50. In one form, the workpiece 60 may be a T-type flow through cell having securing apertures 61 and 62 extending through cell members 63 and 64. An example of such a cell is a "T" flow-cell which may be purchased from Bran Luebbe Corp. of Tarrytown, New York. Securing element 57 may include a screw having a lower threaded portion 65 and a shoulder 66. Securing element 57 extends through securing apertures 61 and 62 and threaded portion 65 engages aperture 51 while shoulder 66 abuts cell member 63. The securing element 57 is rotated a sufficient amount to engage threaded portion 65 with aperture 51 and abut member 63 against friction element 56 and further abut the opposite surface of friction element 56 against friction face 52 of plug 50.

Figure 14:
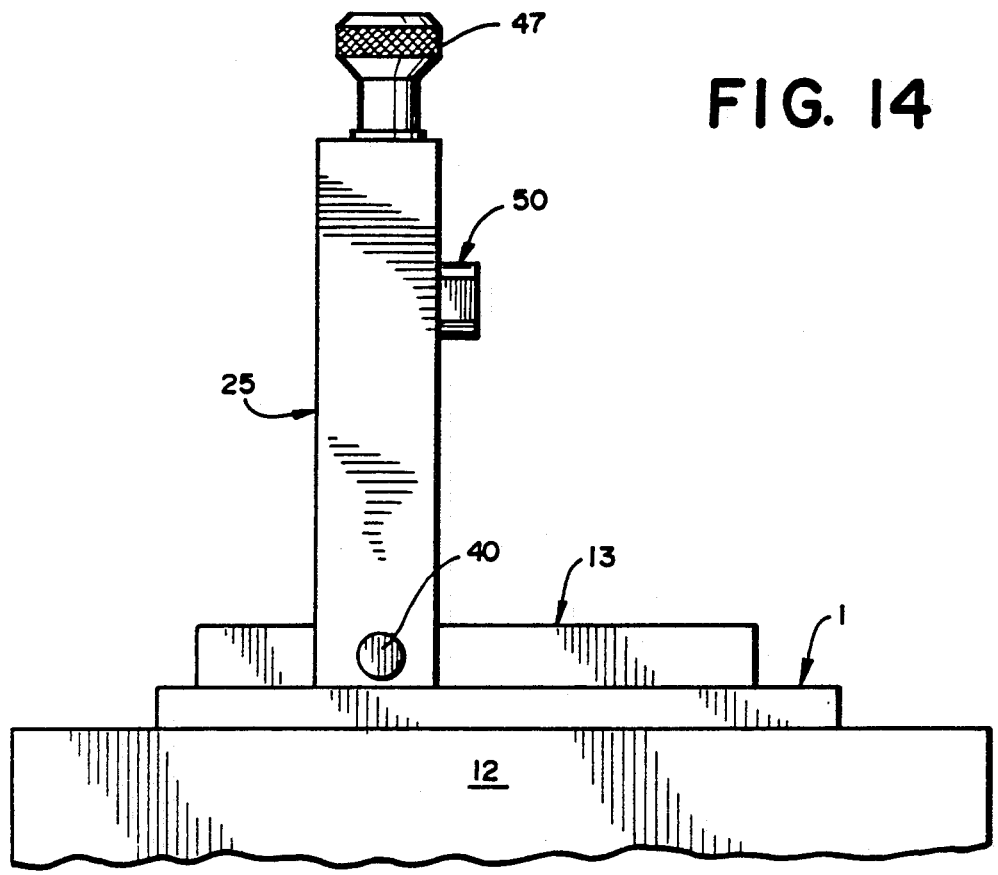
FIG. 14 is a side elevational view of the assembled support device of the present invention.
Figure 15:
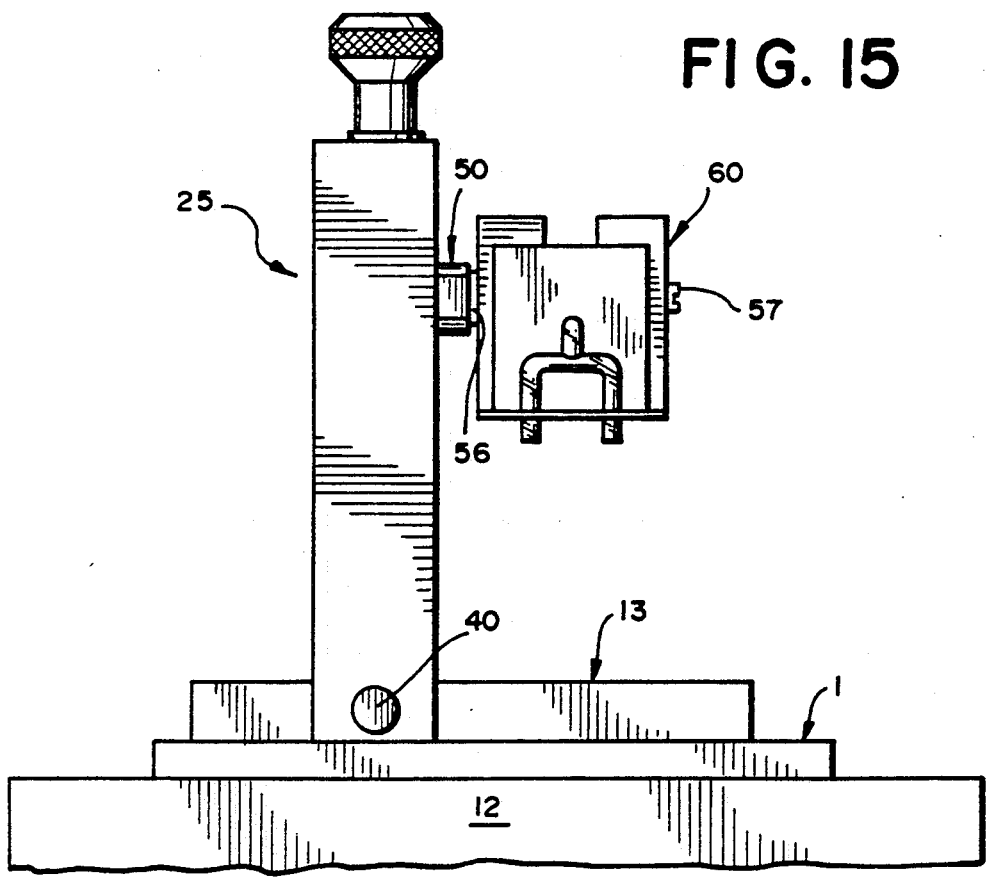
FIG. 15 is a side elevational view of the assembled support device and secured workpiece of the present invention.

The assembled support device, as preferably constructed and mounted, is illustrated in FIGS. 14 and 15. Base plate 1 is connected in any conventional manner to mounting surface 12 which, as illustrated, is horizontal. In one form, the support surface 12 may be a spectrophotometer. Once workpiece 60 is mounted to the device at adjustment plug 50, the position of the workpiece with respect to the support surface 12 can be adjusted linearly along a horizontal or X-axis, linearly along a vertical or Y-axis and a radially about a horizontal axis within the XY plane. The workpiece position is adjusted along a horizontal axis, as illustrated, by rotating set screws 40 and 41 sliding support arm 25 along mounting bar 13. Position adjustment along the vertical or Y axis is made by rotating the adjustment rod 45 via knob 47 thereby moving adjustment plug 50 along the length of elongate cavity 29. Rotational adjustment is made by manually rotating workpiece 60 which by its abutment with friction element 56 maintains the desired orientation.

While the support device of the present invention has been described above in detail, it is to be understood that various changes and modifications may be made without departing from the spirit and scope of the present invention. For example, the base plate 1 may be mounted on any flat surface, be it horizontal, vertical or angular. Further, the force for manipulation of any of the elements by the support device of the present invention may be provided by any conventional source including electronically or mechanically controlled robotics or actuators as well as human energy.

I claim:

1. A support for a spectrophotometric flow cell comprising:
   (a) a base plate, said base plate including a front surface;
   (b) a mounting bar including a back face, said mounting bar mounted on said front surface of said base plate along said back face of said mounting bar;
   (c) a support arm slidably and releasably attached to said mounting bar, said support arm including an elongate cavity and two support legs forming a slot for receiving said mounting bar;
   (d) an adjustment plug; and
   (e) means for locating and adjusting the position of said adjustment plug within said elongate cavity.

2. A support in accordance with claim 1 further comprising means for rotatably friction mounting a workpiece to said adjustment plug.

3. A support in accordance with claim 2 wherein said rotatable friction mounting means includes a friction face on said adjustment plug, a friction element abutting said friction face and means for rotatably abutting said workpiece against said friction element.

4. A support in accordance with claim 3 wherein said abutting means includes a threaded aperture extending inwardly into said adjustment plug and normal to said friction face and a threaded member extending into said threaded aperture in said adjustment plug, said threaded member further including a shoulder for abutting said workpiece against said friction element.

5. A support in accordance with claim 4 wherein said workpiece consists of a T-type, flow-through spectrophotometric cell.

6. A support in accordance with claim 1 wherein said plug locating and adjusting means includes an adjustment rod extending through said elongate cavity and means for mounting said adjustment plug onto said adjustment rod.

7. A support in accordance with claim 6 wherein said adjustment rod extends through and threadedly engages said adjustment plug.

8. A support in accordance with claim 7 further comprising a knob connected to said adjustment rod.

9. A support in accordance with claim 1 wherein said slidably and releasably attaching means includes a threaded aperture formed in each of said support legs and a set screw threadedly engaging each of said threaded apertures and abutting said adjustment rod.

* * * * *